United States Patent
Cavinaw et al.

(10) Patent No.: US 10,301,235 B1
(45) Date of Patent: May 28, 2019

(54) SYSTEMS AND METHODS FOR RECYCLING WASTE PLASTICS, INCLUDING WASTE POLYSTYRENE

(71) Applicant: Agilyx Corporation, Tigard, OR (US)

(72) Inventors: Barry Cavinaw, Wilsonville, OR (US); Sean Crawford, Tigard, OR (US); Sebastien Lamaze, Tigard, OR (US); David Allen, Portland, OR (US); Eric Christenson, Tualatin, OR (US); Mark Rumford, Tigard, OR (US)

(73) Assignee: Agilyx Corporation, Tigard, OR (US)

( * ) Notice: Subject to any disclaimer, the term of this patent is extended or adjusted under 35 U.S.C. 154(b) by 0 days.

(21) Appl. No.: 15/436,541

(22) Filed: Feb. 17, 2017

Related U.S. Application Data

(60) Provisional application No. 62/297,723, filed on Feb. 19, 2016.

(51) Int. Cl.
| | |
|---|---|
| *C07C 4/04* | (2006.01) |
| *C10G 1/10* | (2006.01) |
| *C10G 1/02* | (2006.01) |
| *C10B 53/07* | (2006.01) |
| *C10B 7/06* | (2006.01) |

(52) U.S. Cl.
CPC .............. *C07C 4/04* (2013.01); *C10B 7/06* (2013.01); *C10B 53/07* (2013.01); *C10G 1/02* (2013.01); *C10G 1/10* (2013.01); *C10G 2300/1003* (2013.01)

(58) Field of Classification Search
None
See application file for complete search history.

(56) References Cited

U.S. PATENT DOCUMENTS

| | | | |
|---|---|---|---|
| 2,359,212 A | 9/1944 | Frank et al. | |
| 2,395,829 A | 3/1946 | King | |
| 3,763,015 A | 10/1973 | Morimoto et al. | |
| 3,901,951 A | 8/1975 | Nishizaki | |
| 4,324,643 A * | 4/1982 | Durai-Swamy | C10B 49/20 201/2.5 |
| 5,012,034 A | 4/1991 | Weingaertner et al. | |
| 5,072,068 A | 12/1991 | Luo et al. | |

(Continued)

*Primary Examiner* — Philip Y Louie
(74) *Attorney, Agent, or Firm* — Seed IP Law Group LLP

(57) ABSTRACT

Systems and methods for recycling waste plastics are provided, including a system for recovering styrene monomer from waste polystyrene. The system includes a mixing, heating and compacting apparatus to receive a supply of waste polystyrene and to output a densified polystyrene containing melt; a pyrolysis reactor configured to receive the densified polystyrene containing melt and a supply of recycled oligomers, pyrolyze the densified polystyrene containing melt and the recycled oligomers, and output a hydrocarbon gas stream and a solids residue stream; a quenching apparatus configured to receive the hydrocarbon gas stream output from the pyrolysis reactor and condense out oligomers for routing upstream to the pyrolysis reactor to be combined as the supply of recycled oligomers with the densified polystyrene containing melt, and to discharge an altered hydrocarbon gas stream for further processing; and a condenser configured to receive the altered hydrocarbon gas stream from the quenching apparatus and condense out styrene to form a styrene monomer oil product.

3 Claims, 4 Drawing Sheets

(56) References Cited

U.S. PATENT DOCUMENTS

| | | |
|---|---|---|
| 5,136,117 A | 8/1992 | Paisley et al. |
| 5,300,704 A | 4/1994 | Evans et al. |
| 5,386,070 A | 1/1995 | Evans et al. |
| 5,406,010 A | 4/1995 | Ponsford et al. |
| 5,464,602 A | 11/1995 | Evans et al. |
| 5,672,794 A | 9/1997 | Northemann |
| 5,849,982 A | 12/1998 | Lee et al. |
| 8,449,725 B2 | 5/2013 | Yoon et al. |
| 2007/0227874 A1* | 10/2007 | Wolf-Eberhard ........ C10G 1/10 202/84 |
| 2011/0067992 A1* | 3/2011 | Yoon ........................ C08J 11/12 202/96 |
| 2014/0114098 A1 | 4/2014 | Hofer |

* cited by examiner

SYSTEMS AND METHODS FOR RECYCLING WASTE PLASTICS, INCLUDING WASTE POLYSTYRENE

TECHNICAL FIELD

The present disclosure relates generally to the recycling of waste plastics, including waste polystyrene. Certain embodiments relate more specifically to systems and methods for pyrolyzing plastic feedstocks and recovering the constituent plastic monomers from which they were originally made, including systems and methods to recover styrene from waste polystyrene feedstock.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Certain embodiments of systems and methods described herein are configured for efficient recycling of waste plastics, including waste polystyrene. Some systems and methods can quickly and simply convert waste plastics into one or more purified organic molecular species, which can be considered as a crude hydrocarbon material or crude oil. The crude oil may be readily stored, transported, and/or refined into fuel or other commercially relevant materials. In some instances, a waste polystyrene feedstock can be readily converted into a styrene monomer oil product.

In some embodiments, waste plastic feedstock can be fed continuously through the systems disclosed herein. The feedstock may be pre-melted via a mixing, heating and compacting apparatus prior to introduction into a pyrolysis reactor, which then heats the pre-melted feedstock such that the feedstock transitions into a vapor (e.g., one or more gases) for further processing. In some instances, the vapor can be introduced into a condenser and directly contacted with a pH adjusted solution (or other process solution), which can, in some instances, absorb a portion of the vapor and condense another portion thereof. The condensed material can comprise one or more organic molecular species that can be termed herein as a crude oil. The crude oil can be separated from the other portions of the vapor that are absorbed into the pH adjusted solution, and thus the crude oil can be of a clean or purified quality such that it may be readily refined from its crude state. In other instances, other condensing apparatuses or methodologies may be used to condense out desirable products from the vapor discharged from the pyrolysis reactor.

In some instances, the feedstock may mainly comprise waste polystyrene and the system may be configured to recover a styrene monomer oil product therefrom. In such instances, oligomers may be condensed out of the vapor stream discharged from the pyrolysis reactor and may be routed back to the pyrolysis reactor directly or via a vessel designed to pre-heat and/or thermally treat the oligomer stream. Additionally, after condensing out styrene from the vapor stream, a supplemental condenser may be utilized to condense out light hydrocarbons. The light hydrocarbons can be stored and/or a portion thereof may be used in a quenching apparatus to assist in condensing out the oligomers for re-introduction through the pyrolysis reactor as described above.

Various illustrative embodiments of inventive systems and methods will now be described. Advantages of the systems and methods, as well as features and steps thereof, respectively, will be apparent from the disclosure that follows, including the Figures.

Figure 1:
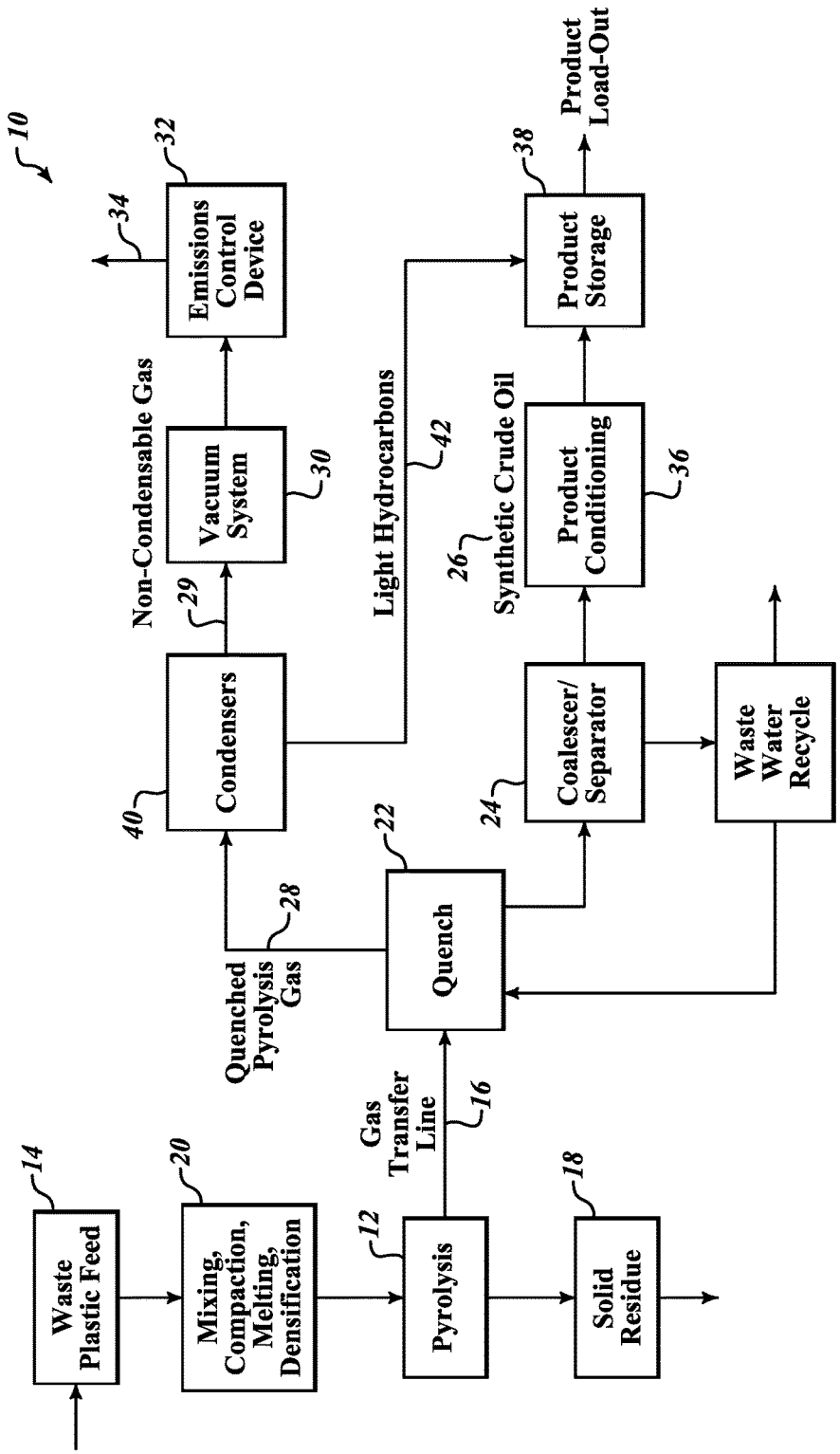
FIG. 1 provides a schematic diagram of an embodiment of a plastic recycling system.

FIG. 1 provides a schematic diagram of an embodiment of a plastic recycling system 10. The plastic recycling system includes a heating system 12 that is configured to deliver heat to a plastic feedstock 14. The heating system 12 can comprise any suitable heating mechanism, such as, for example, a combustion burner, a fluidized bed burner, a retort, or any other such heating system. In some instances, the heating system comprises a pyrolysis recovery unit (PRU). The PRU may include a dual screw feed mechanism to receive the plastic feedstock and simultaneously transport and pyrolyze the feedstock, and to output a hydrocarbon gas stream 16 and a solids residue stream 18. The PRU may include multiple successive zones of heating along a length thereof.

The plastic feedstock 14 can comprise waste plastics of one or more varieties (e.g., mixed plastics), and may include trace amounts of non-plastic contamination or impurities. For example, the impurities may be of an external nature (e.g., water, foodstuffs, labeling, soil, paper, or cellulose waste) or may result from internal amendments (e.g., glass, metal, iron, bromine, and/or chlorine). The plastic feedstock 14 may be provided in a ground, chipped, or other form that can promote the transfer of heat thereto. In some instances, the feedstock 14 may be predominately polystyrene waste.

The plastic feedstock 14 may be fed to the system in a continuous manner. A feed apparatus can include bins, hoppers, conveyors, mixers, heaters and compactors designed to provide a continuous material feed. The feed apparatus may comprise a mixing, heating and compacting apparatus 20 and may include a compactor and a pre-melter, such as a mixer designed to receive the feedstock and output a continuous stream of densified plastic melt. In other instances, the feedstock may be fed directly into the heating system (e.g. PRU) 12 without being subjected to pre-melting.

The heat provided by the heating system (e.g., pyrolysis recovery unit) 12 can be sufficient to crack or depolymerize the plastic feedstock 14 and convert at least a portion thereof into a vapor. The vapor can include one or more gaseous organic species, one or more gaseous inorganic species, and/or one or more varieties of entrained particles. In particular, the vapor can include depolymerized non-polar organic gases, which may be desirable for collection and refinement, and which can be mixed with impurities. The organic gases can include, for example, one or more paraffins, olefins, naphthenes, aromatics, and/or other classes of hydrocarbon materials. The mixed-in impurities can include, for example, inorganic acids (e.g., hydrochloric acid, hydrobromic acid), entrained metals or metalloids (e.g., cadmium, iron, antimony); and/or organic acids (e.g., terephthalic acid). In some embodiments, the vapor may include additional molecular species, such as polar organic molecules, which may or may not be collected with the non-polar organic molecules. For example, the vapor can include one or more alcohols, ketones, ethers, phenols, carboxylic acids, or other polar organic molecules.

In some embodiments, the plastic feedstock may be heated under vacuum conditions, or under negative pressure. In other embodiments, the plastic feedstock may be heated under positive pressure. In still other or further embodiments, the plastic feedstock may be heated under atmospheric pressure conditions, or under any suitable combination of the foregoing (e.g., the pressure may be varied during a heating event).

The vapor can be delivered to a vapor treatment system 22 that effects a phase change of at least a portion of the vapor such that certain molecules transition from a gaseous state to a liquid state. The vapor treatment system 22 may also be referred to as a vapor treatment unit or a vapor treatment vessel. The vapor treatment system 22 may include a pH adjusted solution (or other process solution) that is used to effect the condensation. Moreover, the pH adjusted solution can be configured to absorb at least a portion of the impurities from the vapor. Embodiments of the solution can readily absorb organic acids, inorganic acids, metals, metalloids, and/or certain polar organic molecules. The term "pH adjusted solution" is used in a broad sense and includes solutions that are not pH neutral and that exhibit any or all of the various properties described herein. For example, a pH adjusted solution can be formulated to remove impurities from the vapor, and in further embodiments, can be immiscible with condensed oils so as to be readily separated therefrom. For example, in some embodiments, the pH adjusted solution can comprise an acidic solution, which may, in some cases, be strongly acidic. In further embodiments, the pH adjusted solution can comprise a buffered aqueous solution adjusted to a desired pH value. In various embodiment, the pH adjusted solution can have a pH value that is less than 7, less than about 6.5, less than about 6, less than about 5.5, less than about 5, less than about 4, or less than about 3.

The pH adjusted solution can include one or more chemical amendments of any suitable variety to achieve the desired properties of the solution. Such properties can include, for example, the ability to remove one or more impurities from the vapor and/or a high immiscibility with oil. Adjustment or optimization of one or more of foregoing properties may be achieved by altering the concentration of the one or more chemical amendments within the pH adjusted solution. For example, the presence, combination, and/or concentration of one or more materials within the pH adjusted solution can optimize removal of contaminants from the vapor as it interacts with the pH adjusted solution. In various embodiments, the pH adjusted solution can include strong and/or weak inorganic acids (e.g., hydrochloric acid, acetic acid), one or more pH buffer solutions (e.g., acetic acid+sodium acetate), one or more chelating agents (e.g., ethylenediaminetetraacetic acid (EDTA)), and/or one or more coagulants and/or flocculants (e.g., calcium hydroxide, polyacrylamide).

The vapor treatment system 22 can be configured to effect direct contact between the vapor received therein and the pH adjusted solution (or other process solution). For example, as further discussed below, in some embodiments, the pH adjusted solution may be sprayed into contact with the vapor, whereas in other embodiments, the vapor may be bubbled through the solution. The pH adjusted solution can absorb or dissolve portions of the vapor (e.g., organic acids, inorganic acids, metals, metalloids, and/or certain polar organic molecules). The pH adjusted solution also can be provided at a lower temperature than that of the vapor such that the solution condenses at least those portions of the vapor that are immiscible therein (e.g., non-polar organic molecules).

Those portions of the condensed vapor that are immiscible in the pH adjusted solution (i.e., the hydrophobic portions) can be readily separated from the solution. In some embodiments, the separation (or at least one or more stages thereof) takes place within the vapor treatment system, whereas in other embodiments, the separation (or at least one or more stages thereof) takes place within a separator 24 that is independent of the vapor treatment system 22.

In some embodiments, the immiscible portions are removed from the vapor treatment system as a form of crude oil 26. The crude oil 26 thus can have few or no impurities, as the impurities that were present in the plastic feedstock are dissolved or absorbed into the pH adjusted solution. In some embodiments, at least some of the dissolved or absorbed impurities can remain within the pH adjusted solution within the vapor treatment system 22. For example, in some instances, after the pH adjusted solution has amassed the impurities, it may continue to be used within the vapor treatment system 22, such that the impurities are not removed (at least not immediately) from the vapor treatment system. In other or further embodiments, dissolved or absorbed impurities are removed from the vapor treatment system 22 separately from the oil.

Certain classes of polar organic molecules may only partially (or at least partially) partition into the pH adjusted solution. For example, a portion of certain alcohols, ketones, ethers, phenols, carboxylic acids, and/or other polar organic molecules may partition into the pH adjusted solution and another portion thereof may partition into the crude oil. Accordingly, in some embodiments, crude oil that includes a portion of a species of polar organic molecules may be separated from a pH adjusted solution that contains another portion of the species of polar organic molecules.

The vapor may include portions that do not condense within the vapor treatment system 22 and are not absorbed by the pH adjusted solution. Such non-condensable gases 29 can be removed separately from the vapor treatment system 22, and may be combusted or disposed of in any other suitable manner.

In various embodiments, the vapor treatment system 22 may operate under vacuum conditions, or under negative pressure. In other embodiments, the vapor treatment 22 system may operate under positive pressure. In still other or further embodiments, the vapor treatment system 22 may operate under atmospheric pressure conditions, or under any suitable combination of the foregoing (e.g., the pressure may be varied during a condensing event).

The system can be well suited for quickly cracking or depolymerizing the plastic feedstock. For example, in some embodiments, heating of the plastic feedstock and conversion thereof into the vapor can be performed at high temperatures at which a variety of different molecular species may be gasified simultaneously. Such different molecular species might have different vaporization temperatures at a given pressure, and a temperature at which the plastic feedstock is heated can exceed this temperature for some or all of the molecular species. The molecular species can then be separated from each other when the vapor is delivered to the vapor treatment system, as previously described. Accordingly, the system can operate without the heating system slowly heating up and occasionally holding steady at various discreet temperature levels along the way so as to allow for individual molecular species to be gasified sequentially. It is to be appreciated, however, the system may also be used in an operational mode in which the heating system and the plastic feedstock progress through a series of sequential heating steps or levels, as just described.

The system 10 can include a vacuum system 30 that is configured to maintain a negative pressure within the heating system (e.g., PRU) 12 and within the vapor treatment system 22. The vacuum system 30 can continuously evacuate gases from the heating system (e.g., PRU) 12 such that depolymerization of the plastic feedstock occurs in an oxygen-deprived or oxygen-free environment. The vacuum system 30 draws the vapor into the vapor treatment system 22, where it is contacted by the pH adjusted solution, or non-PH adjusted solution, or otherwise processed by a condensing apparatus or device. The vacuum system 30 draws the non-condensable gases from the vapor treatment system 22, and may distribute them to a combustion unit or other suitable disposal device 32.

The system 10 may include a coalescer/separator 24 that receives an emulsion of condensed material from the vapor treatment system 22. The emulsion can comprise crude oil that includes a small amount of the pH adjusted solution (or other process solution) entrained therein. The coalescer/separator 24 can be configured to separate the crude oil 26 from the pH adjusted solution (or other process solution) based on the difference in relative density between these materials. For example, the coalescer/separator 24 can comprise a settling tank that allows gravitational separation of the solution from the crude oil 26. In other embodiments, the coalescer/separator 24 may comprise a centrifuge or other separator device.

The system 10 can further include a variety of sensor and control components (not shown). For example, the system 10 can include one or more pressure sensors and/or temperature sensors, which can provide to a controller various data regarding the operation of the heating system (e.g., PRU) 12 and the amount of heat being delivered to the feedstock. The sensors can communicate with a controller in any suitable manner, such as by wired or wireless connection. The controller can alter operational parameters of the heating system (e.g., PRU) 12 in response to data received from the sensors and/or as a result of other programming.

A master control system may be configured to communicate with the controller, and may also be configured to communicate with additional controllers that may each be dedicated to subsystems of the plastic recycling system. For example, separate subsystem controllers may be dedicated to the vapor treatment system 22 and the vacuum system 30, respectively. In some embodiments, subsystem controllers may be situated locally (e.g., near the various subsystems with which they are associated), whereas the master control system may be situated in a supervisory station in which an operator can monitor the instantaneous status of the subsystems of the system 10 and make changes thereto as desired, whether onsite or offsite.

For the sake of convenience, subsystem controller(s) associated with a particular component may not be identified hereafter, nor will it be explicitly stated that a particular subsystem controller and/or the master control system is able to monitor and/or control the operation of a particular component of the plastic recycling system 10, although such is understood. It is also noted that steps or control events discussed herein which can be effected by sub-controllers and/or the master control system may be embodied in machine-executable instructions that are to be executed by a general-purpose or special-purpose computer (or other electronic device). Alternatively, the steps or control events may be performed or instigated by hardware components that include specific logic for performing the steps or control events, or by a combination of hardware, software, and/or firmware. Some or all of the steps may be performed locally (e.g., via a subsystem controller) or remotely.

As the feedstock is heated in the heating system (e.g., PRU) 12, the plastic feedstock eventually gasifies or vaporizes. The vapor can be introduced into the vapor treatment system 22 in any suitable manner. For example, in some embodiments, the vapor may be introduced into a condensing tower of a condenser substantially without altering a trajectory of the vapor. In other embodiments, the vapor may encounter a baffle upon entering the condensing tower.

Those portions of the vapor that are not condensed (i.e., non-condensable gases) may be passed to a caustic scrubber, which passes the remaining vapor through a caustic solution so as to chemically scrub the vapor (e.g., remove mercaptan sulfur species therefrom) and so as to neutralize trace levels of free inorganic acids. The remainder of the vapor may pass from the caustic scrubber through to an emissions control device (ECD) 32. Any suitable vacuum system 30 may be used with the plastic recycling system 10 to move the vapor accordingly.

Any suitable emissions control device (ECD) 32 can be used with the plastic recycling system 10. In some embodiments, the emissions control device 32 can comprise a burner or other combustion device. Exhaust 34 from the emissions control device 32 may be vented to atmosphere. In other embodiments, the hot exhaust 34 may instead be transferred to other portions of the plastic recycling system 10.

The absorbed and condensed portions of the vapor may settle into a tank of the coalescer/separator 24 that includes one or more weirs. The pH adjusted solution (or other process solution), which retains the absorbed impurities, may facilitate coagulation of some contaminants which have a greater relative density than the condensed crude oil material 26, and may settle to the bottom of the tank. Accordingly, the condensed crude oil 26 rises to the top of the tank and flows over the one or more weirs to be collected for further processing 36, storage 38 or use.

In addition, downstream processing may be provided in some embodiments to purify the product streams discussed herein or fractionate said streams into specified hydrocarbon cuts. Process units for this purpose may include, but are not limited to, distillation, solvent extraction, adsorption, and catalyst treatment units.

In some instances, one or more supplemental condensers 40 may be provided to condense out light hydrocarbons 42 from the quenched pyrolysis gas 28. The one or more streams of light hydrocarbons 42 may then be combined with the crude oil product 26, or may be stored as separate hydrocarbon products.

Figure 2:
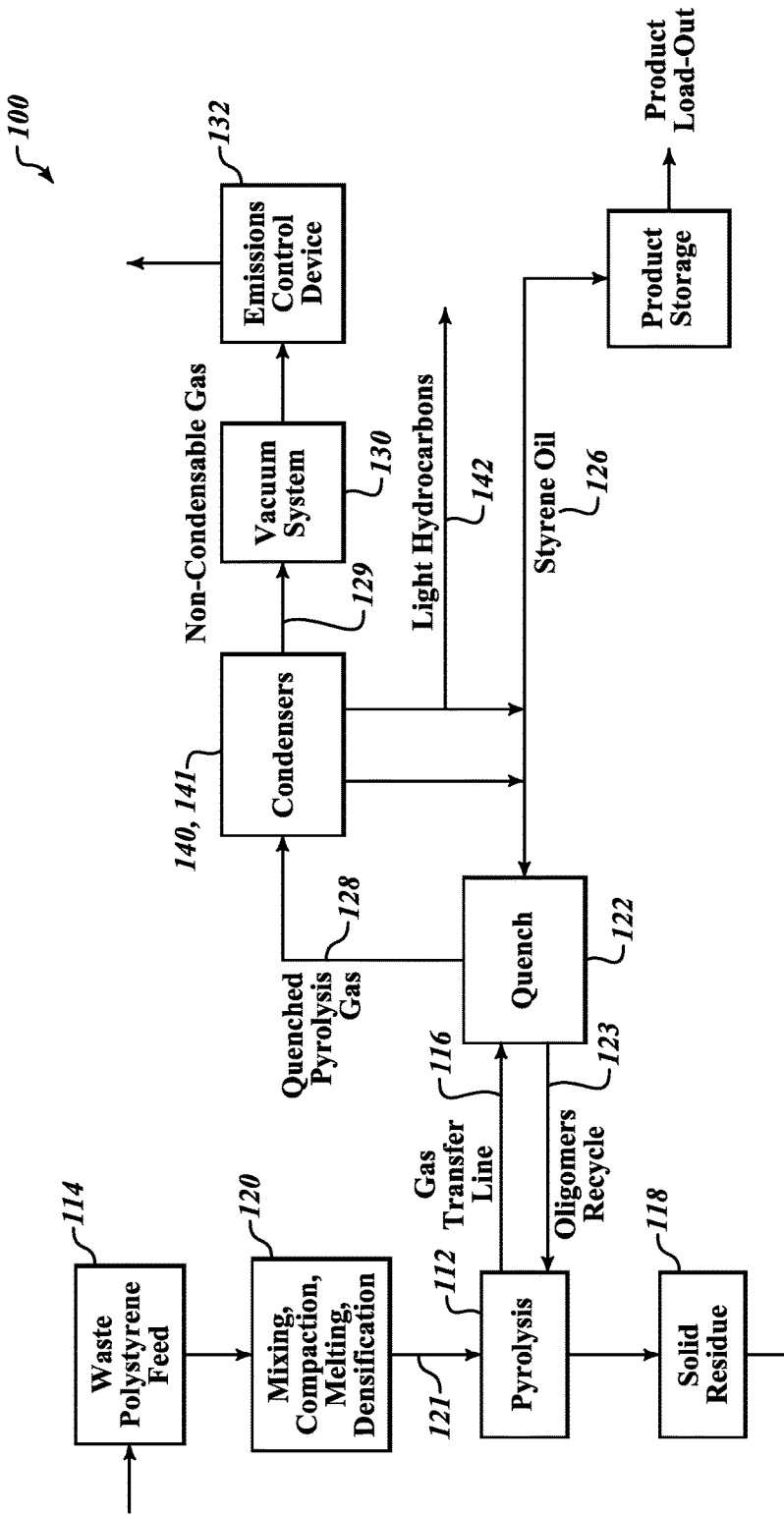
FIG. 2 provides a schematic diagram of another embodiment of a plastic recycling system.
Figure 3A:
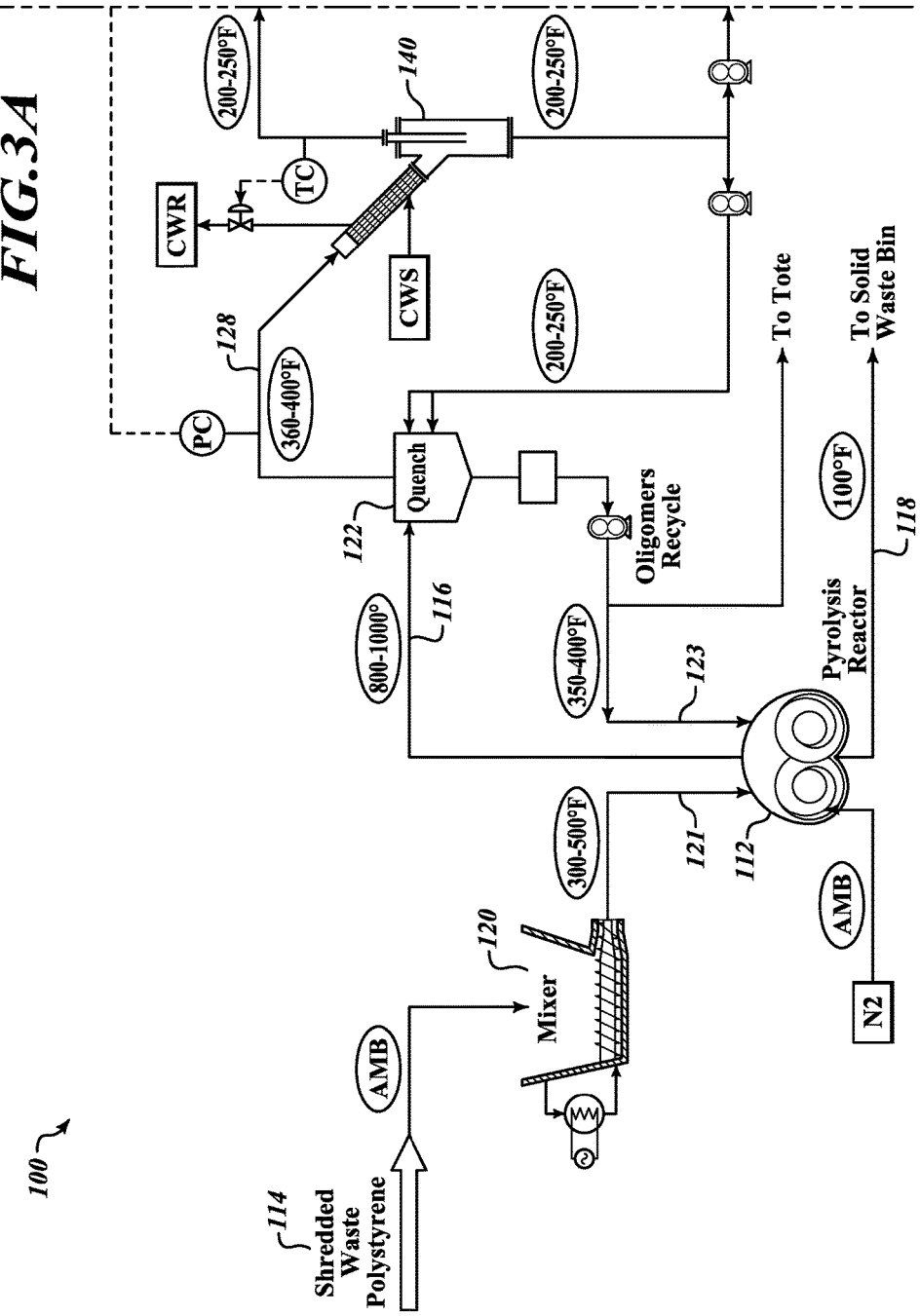
FIGS. 3A and 3B provide another schematic diagram of the plastic recycling system of FIG. 2.
Figure 3B:
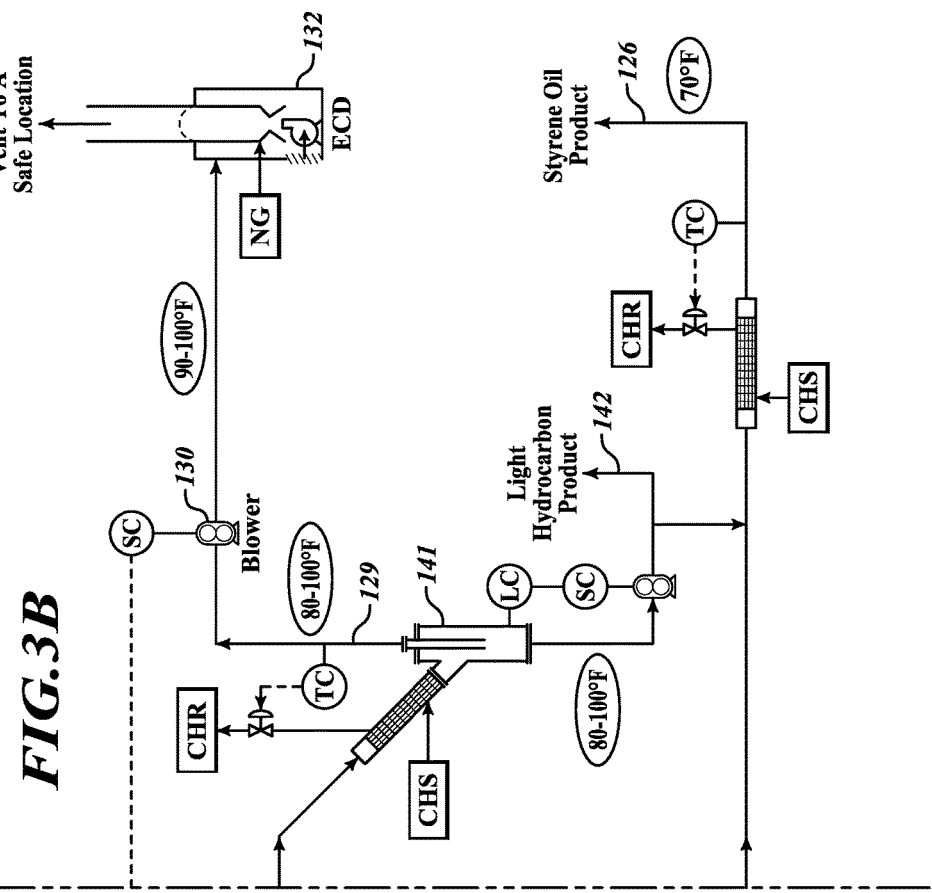

FIG. 2 and FIGS. 3A and 3B provide schematic diagrams of another embodiment of a plastic recycling system 100, which is particularly well suited for producing a styrene monomer oil product 126 from waste polystyrene 114. Similar to the aforementioned system, a mixing, heating and compacting apparatus (e.g., a mixer) 120 may be provided to receive a supply of waste polystyrene 114 and to output a densified polystyrene containing melt 121. The system 100 may further include a pyrolysis recovery unit (PRU) 112 that is configured to receive the densified polystyrene containing melt 121 and pyrolyze the densified polystyrene containing melt 121 and output a hydrocarbon gas stream 116 and a solids residue stream 118. The PRU 112 may comprise, for example, a dual screw feed mechanism within a reactor shell which is configured to simultaneously transport and heat the feedstock introduced into the PRU 112. The PRU 112 may have multiple zones of heating along a length thereof to effectively heat the feedstock to a pyrolysis temperature as the material progresses from one end of the PRU 112 to the other.

The system 100 may further comprise a quenching apparatus 122 that is configured to receive the hydrocarbon gas stream 116 output from the PRU 112 and to condense out oligomers (e.g., dimers and trimers) 123 for routing upstream to the PRU 112. In this manner, a portion of the feedstock can be continuously refined to provide an exceptionally purified styrene monomer oil product. The quenching apparatus 122 may also be configured to discharge an altered hydrocarbon gas stream 128 for further processing. A condenser 140 may be provided to receive the altered hydrocarbon gas stream 128 from the quenching apparatus 122 and to condense out styrene to form the styrene monomer oil product 126. Additionally, a supplemental condenser 141 may be provided to receive a discharged gas stream from the styrene condenser 140 and to condense out light hydrocarbons 142 which may form a light hydrocarbon product or may be combined with other streams. The supplemental condenser 141 may be configured to direct a portion of the light hydrocarbons 142 upstream to the quenching apparatus 122 to assist in condensing out the oligomers 123 from the hydrocarbon gas stream 116 output from the PRU 112. Any remaining non-condensable gasses 129 may be processed as described in connection with the aforementioned system, including processing by an appropriate emissions control device 132 and under the influence of a vacuum system 130.

In addition, downstream processing may be provided in some embodiments to purify the product streams discussed herein or fractionate said streams into specified hydrocarbon cuts. Process units for this purpose may include, but are not limited to, distillation, solvent extraction, adsorption, and catalyst treatment units.

FIGS. 3A and 3B provide a schematic flow diagram of aspects and functionalities of system 100 with representative temperature data. The schematic flow diagram includes various industry standardized piping and instrument diagram symbols and abbreviations, including, for example, the abbreviations AMB, PC, CWS, TC, CWR, CHS, CHR, ECD, LC, and SC, wherein: AMB means ambient temperature; PC means pressure controller; CWS means cooling water supply; TC means temperature controller; CWR means cooling water return; CHS means chilled water supply; CHR means chilled water return; ECD means emissions control device; LC means level controller; and SC means speed controller.

Additional components, features and functionality of the systems will be readily apparent to those of ordinary skill in the relevant art upon a review of the detailed schematic diagrams provided in the Figures.

Moreover, it will be understood by those having ordinary skill in the relevant art that changes may be made to the details of the embodiments described and illustrated herein without departing from the underlying principles presented herein. For example, any suitable combination of various embodiments, or the features thereof, is contemplated. For example, various embodiments may be configured to operate in one or more of a batch mode, a continuous batch mode, or a continuous mode. Other or further embodiments may include a condenser system and/or other components that are configured to operate under one or more of vacuum conditions, atmospheric pressure conditions, or positive pressure conditions.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

CROSS-REFERENCE TO RELATED APPLICATION

This application claims the benefit of U.S. Provisional Application No. 62/297,723, filed Feb. 19, 2016, which is incorporated herein by reference in its entirety.

The invention claimed is:

1. A method of recovering styrene monomer from waste polystyrene, the method comprising:
    mixing, heating and compacting a supply of waste polystyrene to form a densified polystyrene containing melt;
    supplying the densified polystyrene containing melt to a pyrolysis reactor along with a supply of recycled oligomers;
    pyrolyzing the densified polystyrene containing melt and recycled oligomers within the pyrolysis reactor to generate a hydrocarbon gas stream and a solids residue stream;
    condensing out oligomers from the hydrocarbon gas stream output from the pyrolysis reactor with a quenching apparatus and routing the oligomers upstream to the pyrolysis reactor to be combined as the supply of recycled oligomers with the densified polystyrene containing melt;
    discharging an altered hydrocarbon gas stream from the quenching apparatus;
    condensing out styrene from the altered hydrocarbon gas stream with a primary condenser to form a styrene monomer oil product and a discharged gas stream;
    condensing out a hydrocarbon fraction from the discharged gas stream with a secondary condenser; and
    directing a stream of hydrocarbons from the hydrocarbon fraction output from the secondary condenser upstream to the quenching apparatus to assist in condensing out the oligomers from the hydrocarbon gas stream output from the pyrolysis reactor.

2. The method of claim 1, wherein the densified polystyrene containing melt is supplied to the pyrolysis reactor in a continuous manner.

3. The method of claim 1, wherein pyrolyzing the densified polystyrene containing melt and recycled oligomers within the pyrolysis reactor includes simultaneously transporting and heating the densified polystyrene containing melt and recycled oligomers with a dual screw feed mechanism.

\* \* \* \* \*